(12) United States Patent
Kaji et al.

(10) Patent No.: US 10,874,329 B2
(45) Date of Patent: Dec. 29, 2020

(54) THREE-DIMENSIONAL MEASUREMENT METHOD AND THREE-DIMENSIONAL MEASUREMENT DEVICE

(71) Applicant: J. MORITA MFG. CORP., Kyoto (JP)

(72) Inventors: Ryosuke Kaji, Kyoto (JP); Mikinori Nishimura, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 121 days.

(21) Appl. No.: 16/016,100

(22) Filed: Jun. 22, 2018

(65) Prior Publication Data

US 2018/0296131 A1 Oct. 18, 2018

Related U.S. Application Data

(63) Continuation of application No. PCT/JP2016/088538, filed on Dec. 22, 2016.

(30) Foreign Application Priority Data

Dec. 24, 2015 (JP) .................................. 2015-251341

(51) Int. Cl.
*A61B 5/107* (2006.01)
*A61C 19/04* (2006.01)
(Continued)

(52) U.S. Cl.
CPC .......... *A61B 5/1077* (2013.01); *A61B 5/0088* (2013.01); *A61B 5/1079* (2013.01);
(Continued)

(58) Field of Classification Search
CPC ... A61B 5/1077; A61B 5/7425; A61B 5/7221; A61B 5/1079; A61B 5/0088; G01B 21/20; G01B 11/24; A61C 19/04
See application file for complete search history.

(56) References Cited

U.S. PATENT DOCUMENTS

| 2013/0162645 A1 | 6/2013 | Ulrici |
| 2015/0072313 A1 | 3/2015 | Thiel et al. |

(Continued)

FOREIGN PATENT DOCUMENTS

| JP | 2003-148934 A | 5/2003 |
| JP | 2008-537494 A | 9/2008 |

(Continued)

OTHER PUBLICATIONS

Extended European Search Report dated Jun. 14, 2019 in Patent Application No. 16879002.0, 5 pages.

(Continued)

*Primary Examiner* — Nam D Pham
(74) *Attorney, Agent, or Firm* — Oblon, McClelland, Maier & Neustadt, L.L.P.

(57) ABSTRACT

A method of three-dimensional measurement in an oral cavity includes conducting three-dimensional measurement on a measurement range in an oral cavity, detecting a measurement site in which measurement information is insufficient in a measurement result acquired in the three-dimensional measurement, notifying a start position at which re-measurement on the measurement site detected is to be started, re-measuring an area starting from the start position such that the area encompasses the measurement site, and adapting at least one characteristic site having characteristic information in a re-measurement result from the re-measuring, and at least one characteristic site having characteristic information in the measurement result from the three-dimensional measurement with respect to each other such that three-dimensional measurement information is created on the measurement range.

22 Claims, 11 Drawing Sheets

(51) Int. Cl.
  *G01B 11/24* (2006.01)
  *G01B 21/20* (2006.01)
  *A61B 5/00* (2006.01)
(52) U.S. Cl.
  CPC .......... *A61B 5/7221* (2013.01); *A61B 5/7425* (2013.01); *A61C 19/04* (2013.01); *G01B 11/24* (2013.01); *G01B 21/20* (2013.01)

(56) References Cited

U.S. PATENT DOCUMENTS

2015/0206306 A1* 7/2015 Adamson ............. A61C 9/0053
  433/215
2017/0243381 A1 8/2017 Ulrici

FOREIGN PATENT DOCUMENTS

| JP | 2012-245064 A | 12/2012 |
| JP | 2015-524724 A | 8/2015 |

OTHER PUBLICATIONS

International Search Report dated Mar. 21, 2017 in PCT/JP2016/088538, filed Dec. 22, 2016, 4 pages with English Translation.
Japanese Office Action dated May 26, 2020 in Japanese Patent Application No. 2017-558302 (with English translation), 6 pages.
Office Action dated May 11, 2020 in corresponding European Patent Application No. 16 879 002.0, 7 pages.

* cited by examiner

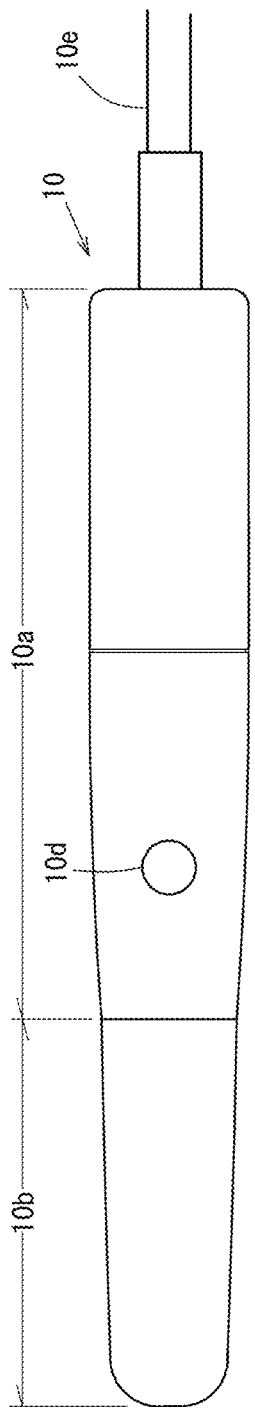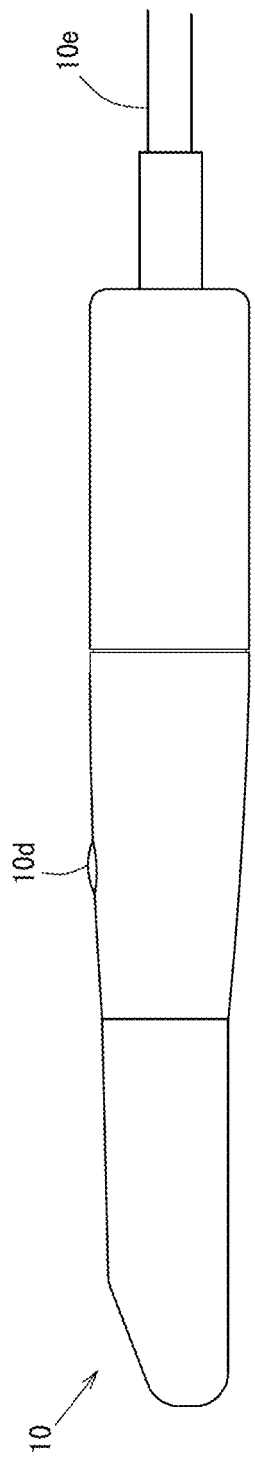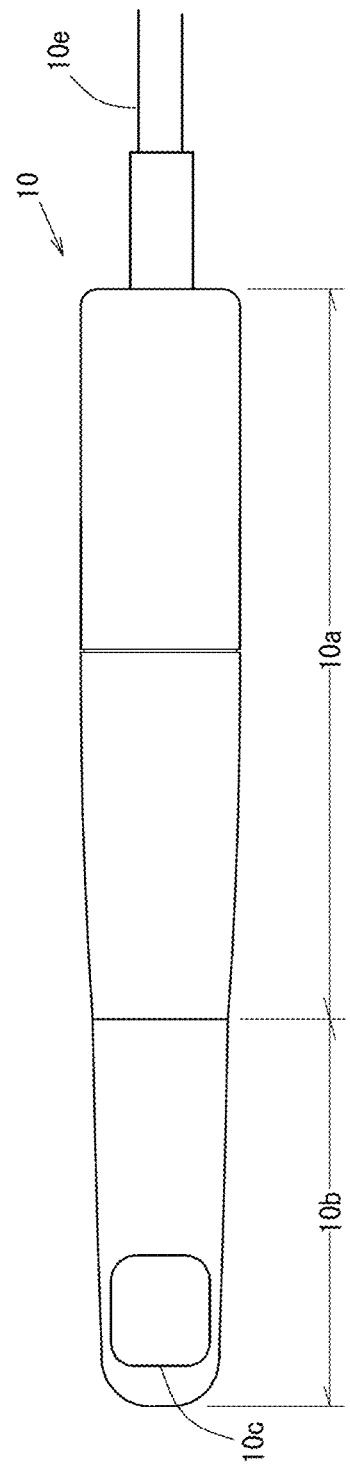

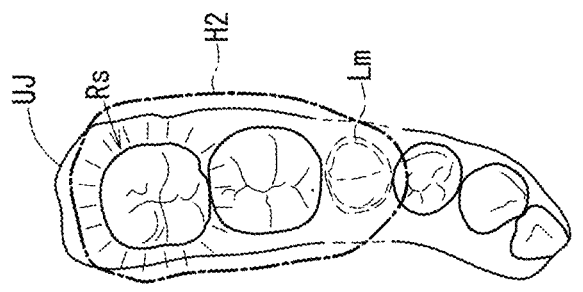
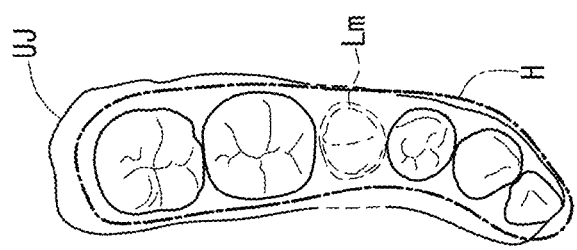
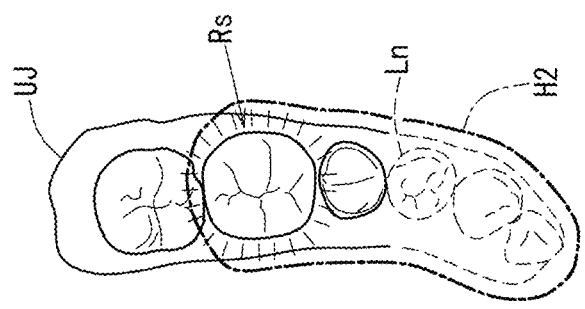
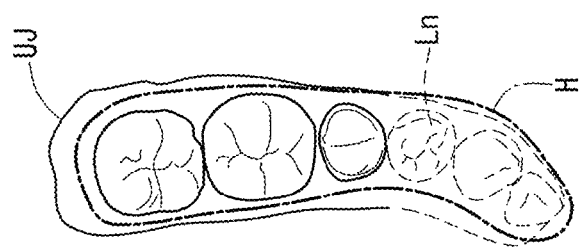
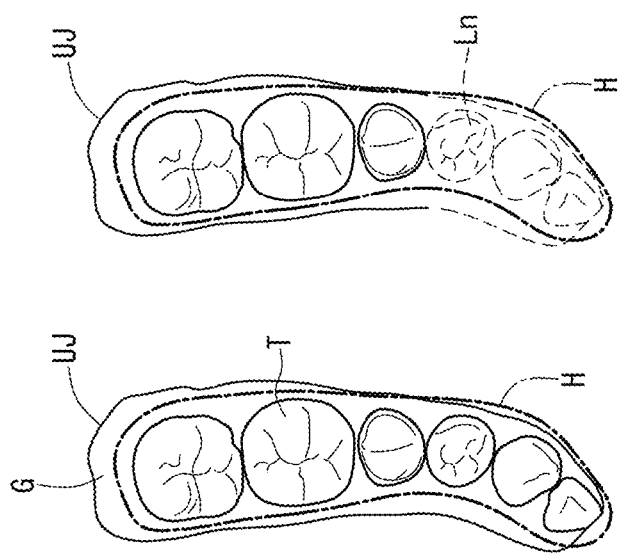

FIG. 11
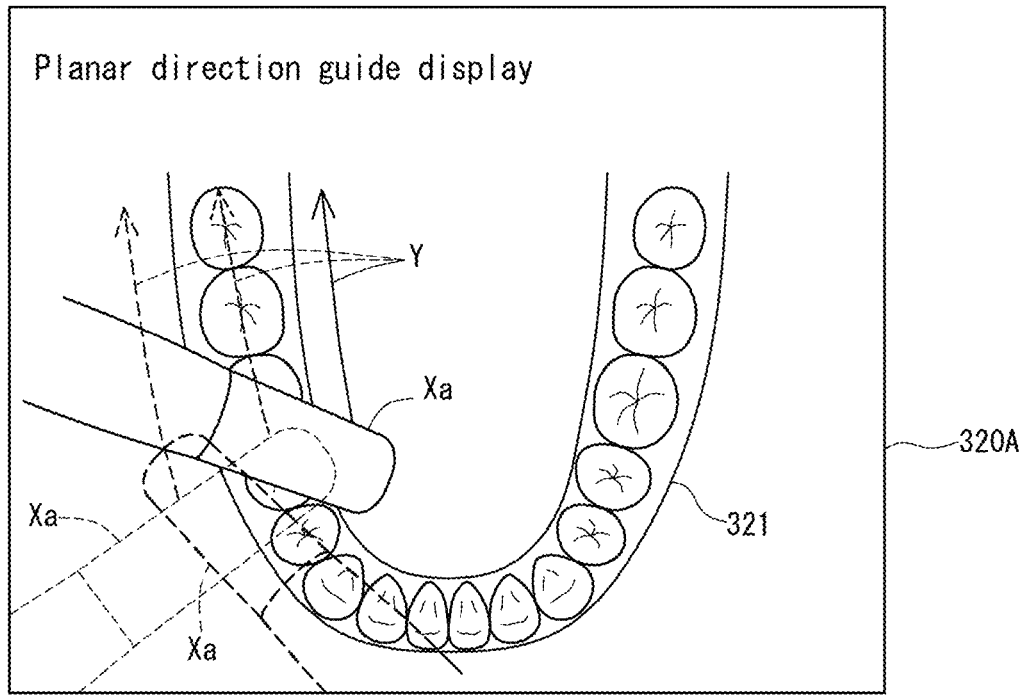
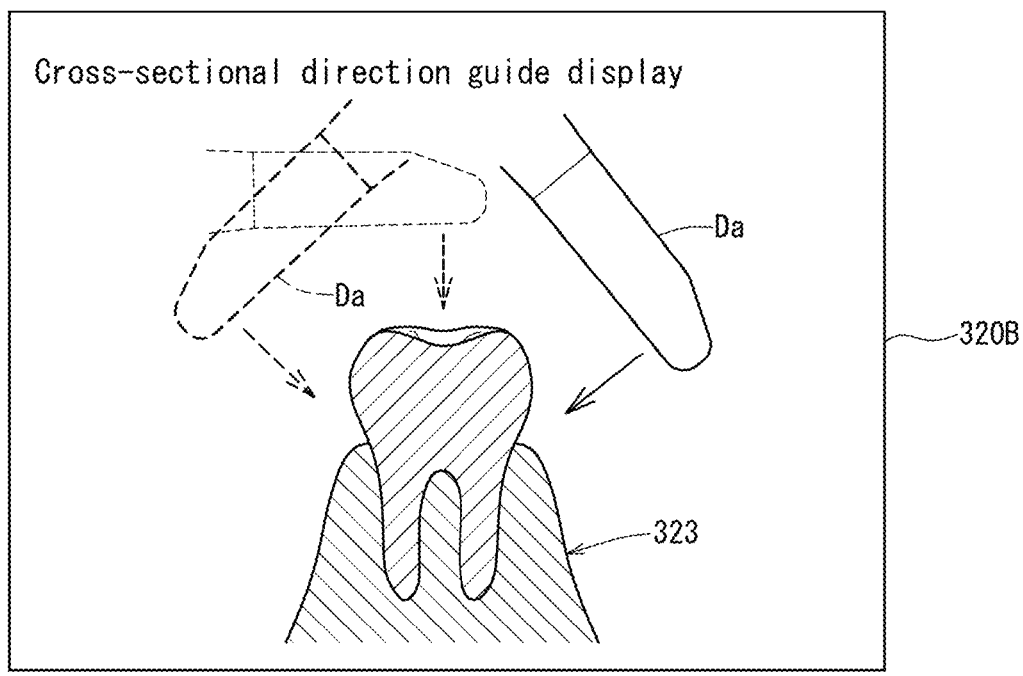

THREE-DIMENSIONAL MEASUREMENT METHOD AND THREE-DIMENSIONAL MEASUREMENT DEVICE

CROSS-REFERENCE TO RELATED APPLICATIONS

The present application is a continuation of and claims the benefit of priority to International Application No. PCT/JP2016/088538, filed Dec. 22, 2016, the entire contents of which are incorporated herein by reference. PCT/JP2016/088538 is based upon and claims the benefit of priority to Japanese Application No. 2015-251341, filed Dec. 24, 2015. The present application claims the benefit of priority to Japanese Application No. 2015-251341.

TECHNICAL FIELD

The present invention relates to a three-dimensional measurement method and a three-dimensional measurement device for scanning an oral cavity to measure a three-dimensional shape of a measurement target site.

BACKGROUND ART

For example, Japanese PCT National-Phase Patent Laid-Open Publication No. 2008-537494 proposes a measurement system that guides the order or the direction of scanning for a measurement target site. Especially, the measurement system described in Japanese PCT National-Phase Patent Laid-Open Publication No. 2008-537494 allows the measurement to be performed easily by performing scanning along with the guide. The entire contents of this publication are incorporated herein by reference.

SUMMARY OF INVENTION

According to one aspect of the present invention, a method of three-dimensional measurement in an oral cavity includes conducting three-dimensional measurement on a measurement range in an oral cavity, detecting a measurement site in which measurement information is insufficient in a measurement result acquired in the three-dimensional measurement, notifying a start position at which re-measurement on the measurement site detected is to be started, re-measuring an area starting from the start position such that the area encompasses the measurement site, and adapting at least one characteristic site having characteristic information in a re-measurement result from the re-measuring, and at least one characteristic site having characteristic information in the measurement result from the three-dimensional measurement with respect to each other such that three-dimensional measurement information is created on the measurement range.

According to another aspect of the present invention, a three-dimensional measurement apparatus for an oral cavity includes a three-dimensional measurement device that conducts three-dimensional measurement on a measurement range in an oral cavity, computation processing circuitry that detects a measurement site in which measurement information is insufficient in a measurement result acquired by the three-dimensional measurement device, and output circuitry that notifies a start position at which re-measurement on the measurement site detected is to be started. The computation processing circuitry adapts at least one characteristic site having characteristic information in a re-measurement result from the re-measurement by the three-dimensional measurement device on an area starting from the start position and encompassing the measurement site, and at least one characteristic site having characteristic information in the measurement result from the three-dimensional measurement with respect to each other such that three-dimensional measurement information is created on the measurement range.

BRIEF DESCRIPTION OF DRAWINGS

A more complete appreciation of the invention and many of the attendant advantages thereof will be readily obtained as the same becomes better understood by reference to the following detailed description when considered in connection with the accompanying drawings, wherein:

FIG. 3A-3C show a three-dimensional measurement tool;

FIG. 6A-6E schematically show measurement information-insufficient sites;

FIG. 11 shows a guide display portion in a three-dimensional measurement screen in another embodiment.

DESCRIPTION OF EMBODIMENTS

Figure 1:
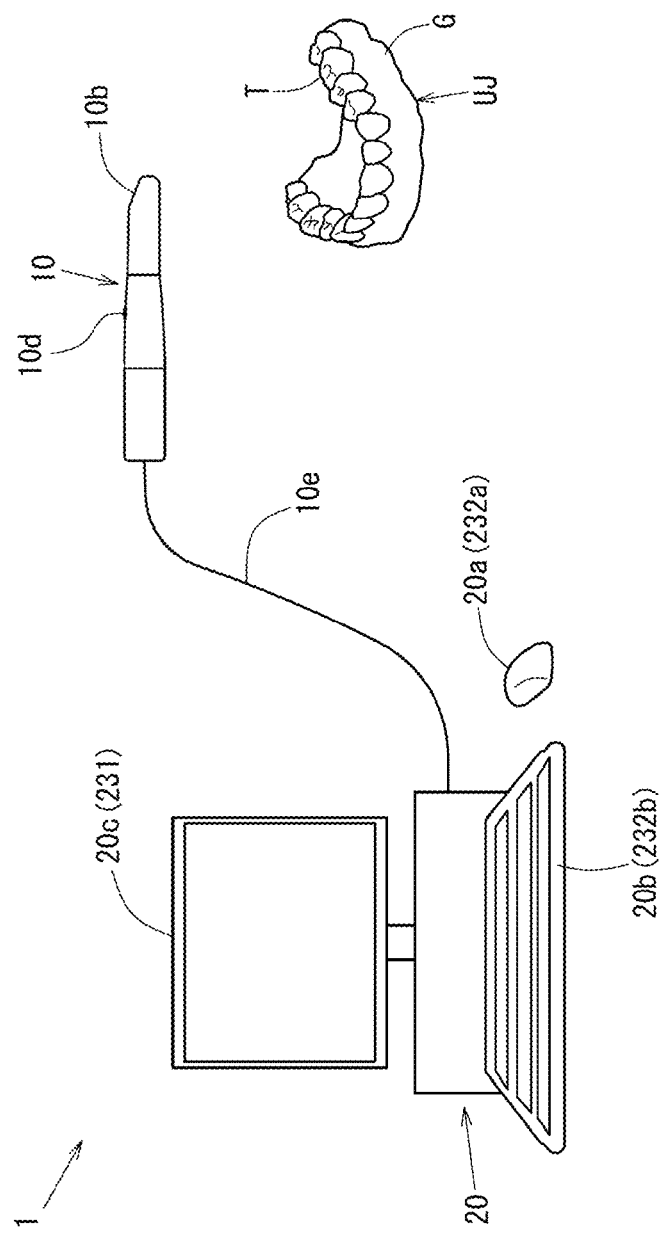
FIG. 1 is a schematic view of a three-dimensional measurement system.

Embodiments will now be described with reference to the accompanying drawings, wherein like reference numerals designate corresponding or identical elements throughout the various drawings.

Figure 2:
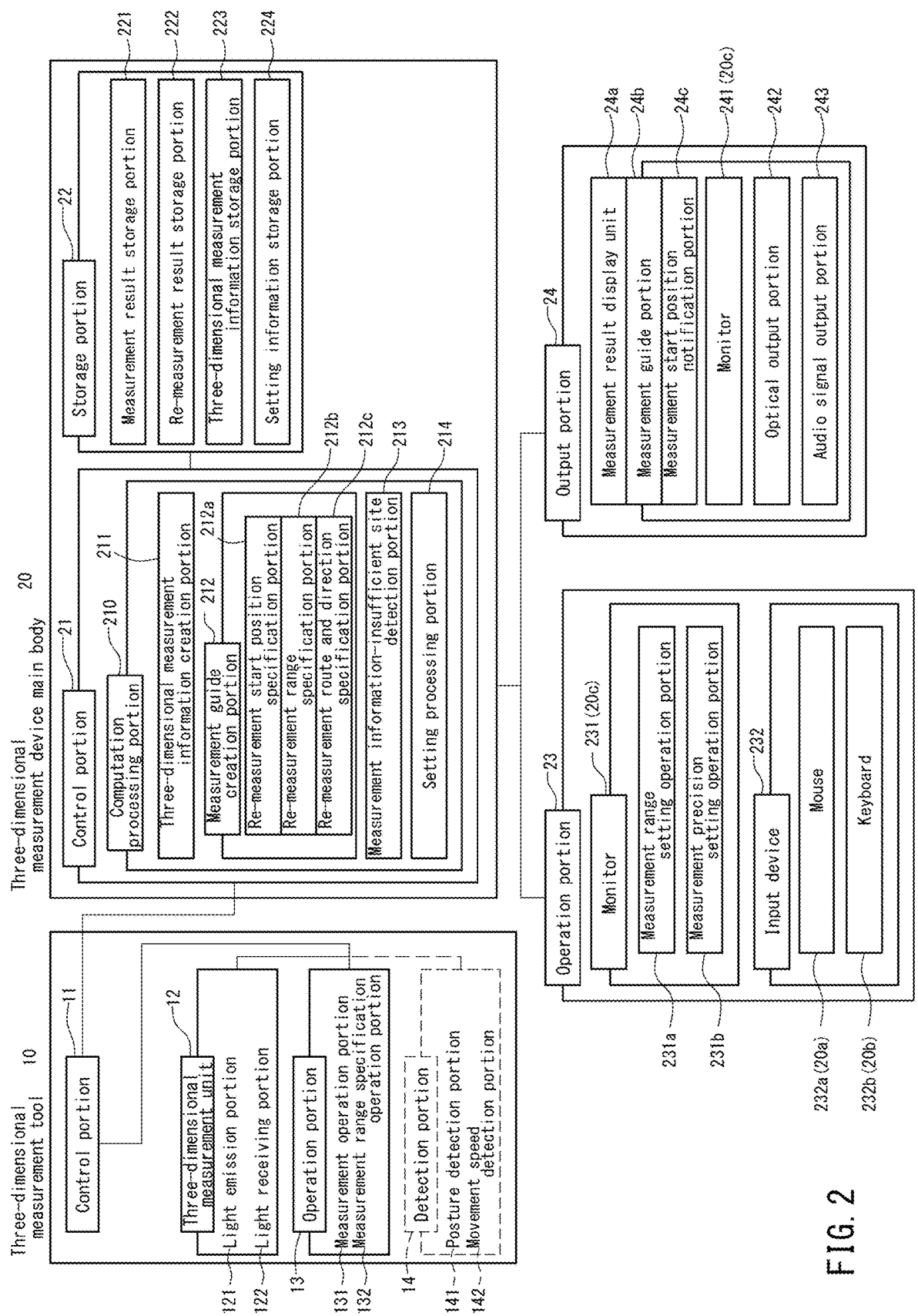
FIG. 2 is a block diagram of the three-dimensional measurement system.

FIG. 1 is a schematic view of a three-dimensional measurement system 1. FIG. 2 is a block diagram of the three-dimensional measurement system 1. FIG. 3 shows a scanner 10. In more detail, FIG. 3(a) is a plan view of the scanner 10, FIG. 3(b) is front view of the scanner 10, and FIG. 10(c) is a bottom view of the scanner 10.

Figure 4:
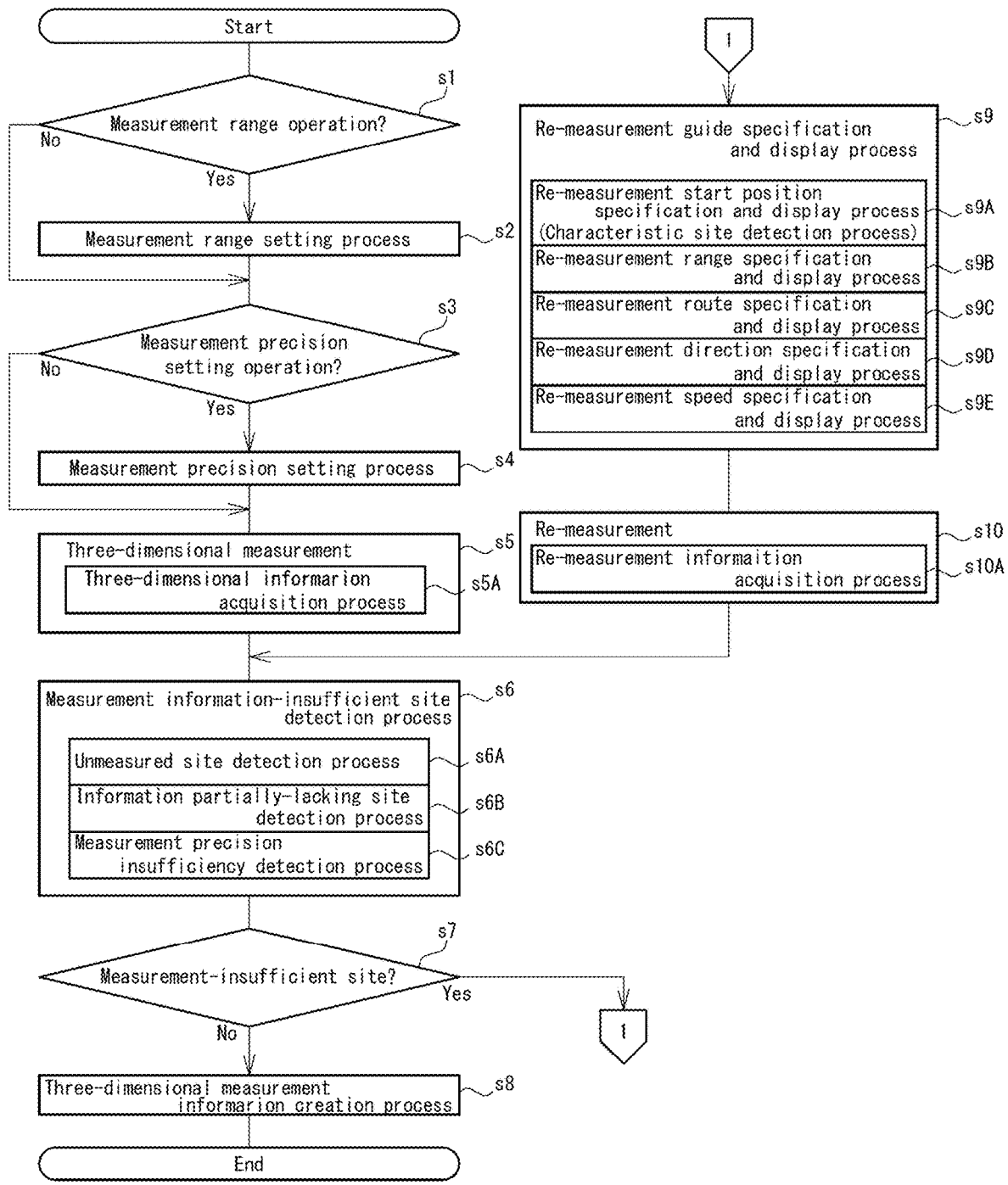
FIG. 4 is a flowchart of three-dimensional measurement.

FIG. 4 is a flowchart of three-dimensional measurement performed by use of the three-dimensional system 1. FIG. 5 provides schematic views showing the three-dimensional measurement. FIG. 6 provides schematic views showing measurement information-insufficient sites Lm and Ln.

Figure 5A:
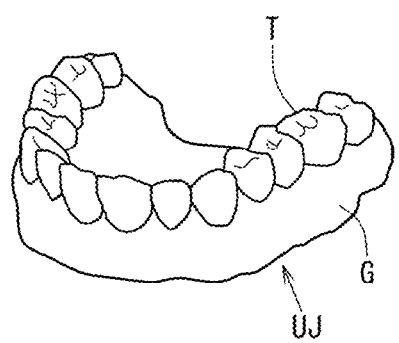
FIG. 5A-5D schematically show the three-dimensional measurement.
Figure 5C:
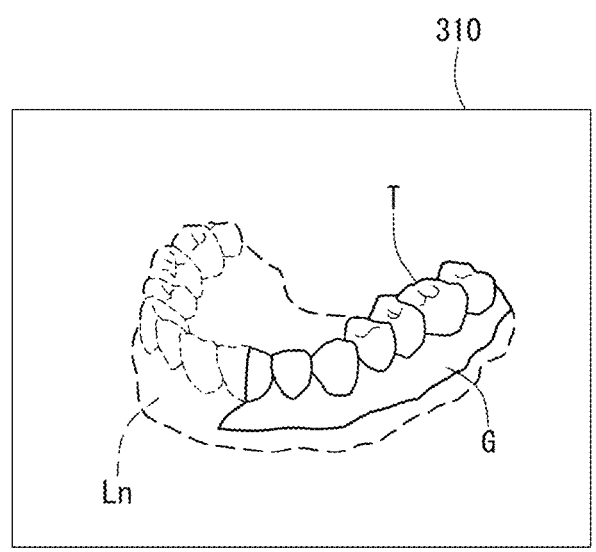
Figure 5B:
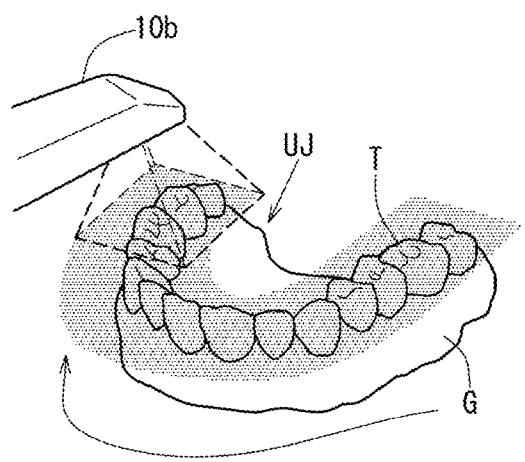
Figure 5D:
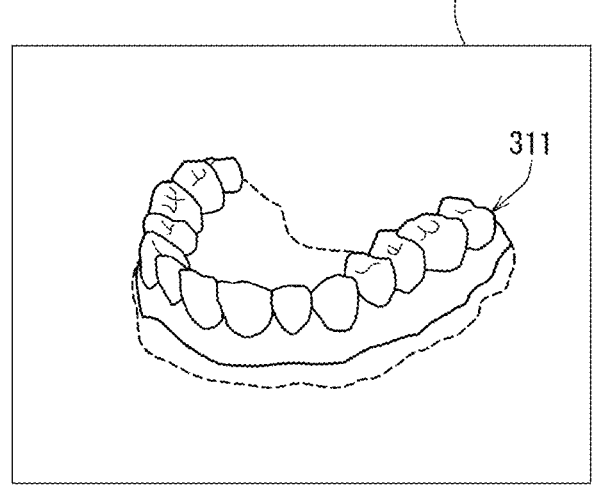

In more detail, FIG. 5(a) is a schematic perspective view of an under jaw UJ, which is a measurement target. FIG. 5(b) is a schematic perspective view showing that the lower jaw UJ is scanned by the scanner 10 from the left molar tooth to the right molar tooth via front teeth. FIG. 5(c) shows a three-dimensional measurement image 311 of a state where approximately the left half of the lower jaw UJ has been measured by the scanner 10. FIG. 5(d) shows the three-dimensional measurement image 311 of a state where the measurement on the lower jaw UJ by the scanner 10 has been finished.

In FIG. 5(c) and FIG. 5(d), a site that is encompassed in a measurement range H but has not been measured (hereinafter, referred to as an "unmeasured site Ln") is represented with the dashed line for the sake of convenience.

FIG. 6(a) is a plan view of the measurement range H in the lower jaw UJ. FIG. 6(b) is an image showing a measurement result in which the unmeasured site Ln is represented with the dashed line. FIG. 6(c) is a plan view showing a re-measurement start position Rs and a re-measurement range H2 provided as guide displays for the unmeasured site Ln. FIG. 6(d) is an image showing a measurement result in which an information partially-lacking site Lm is represented with the dashed line. FIG. 6(e) is a plan view showing the re-measurement start position Rs and the re-measurement range H2 provided as guide displays for the information partially-lacking site Lm.

Figure 7:
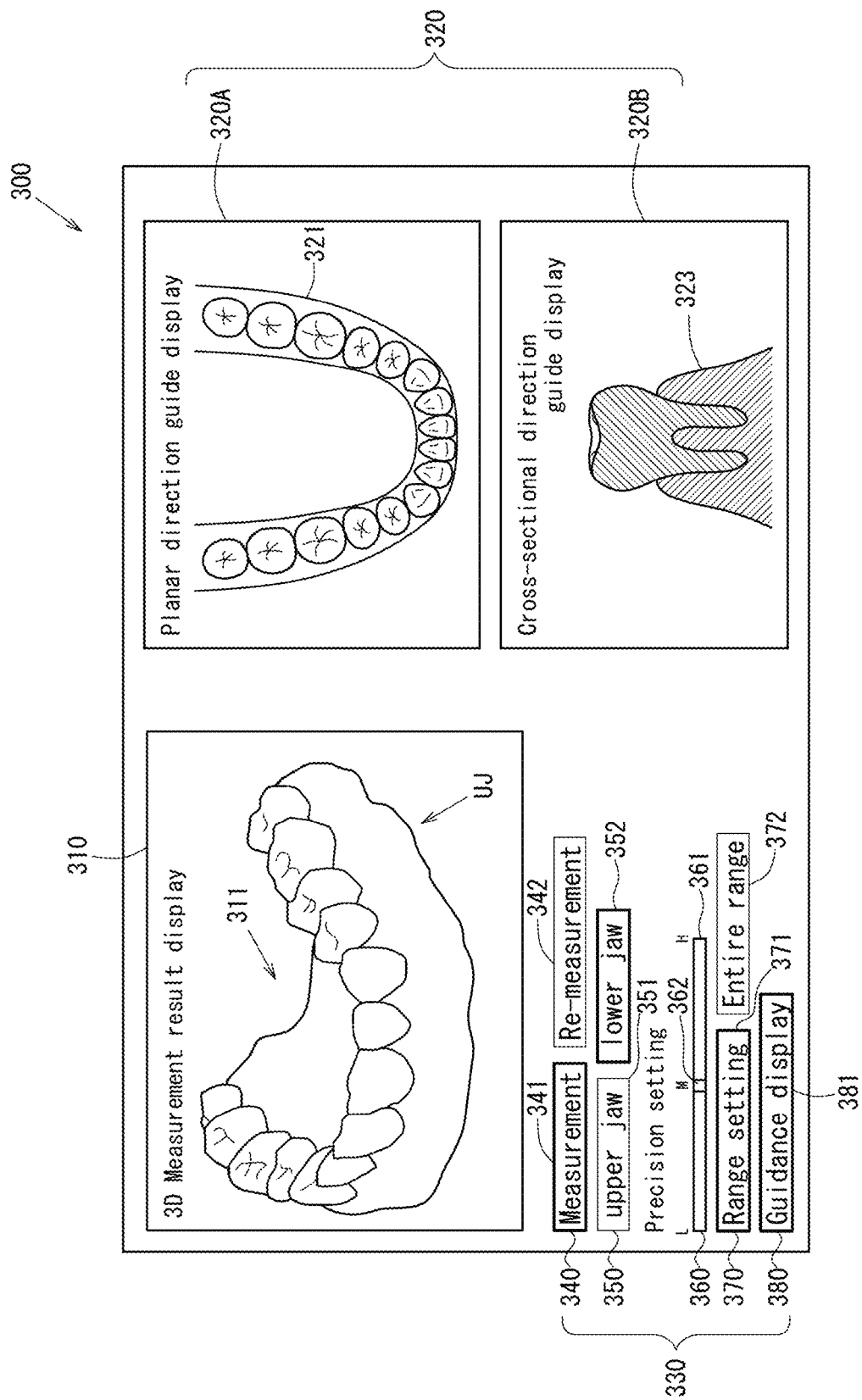
FIG. 7 is a schematic view of a three-dimensional measurement screen.
Figure 8:
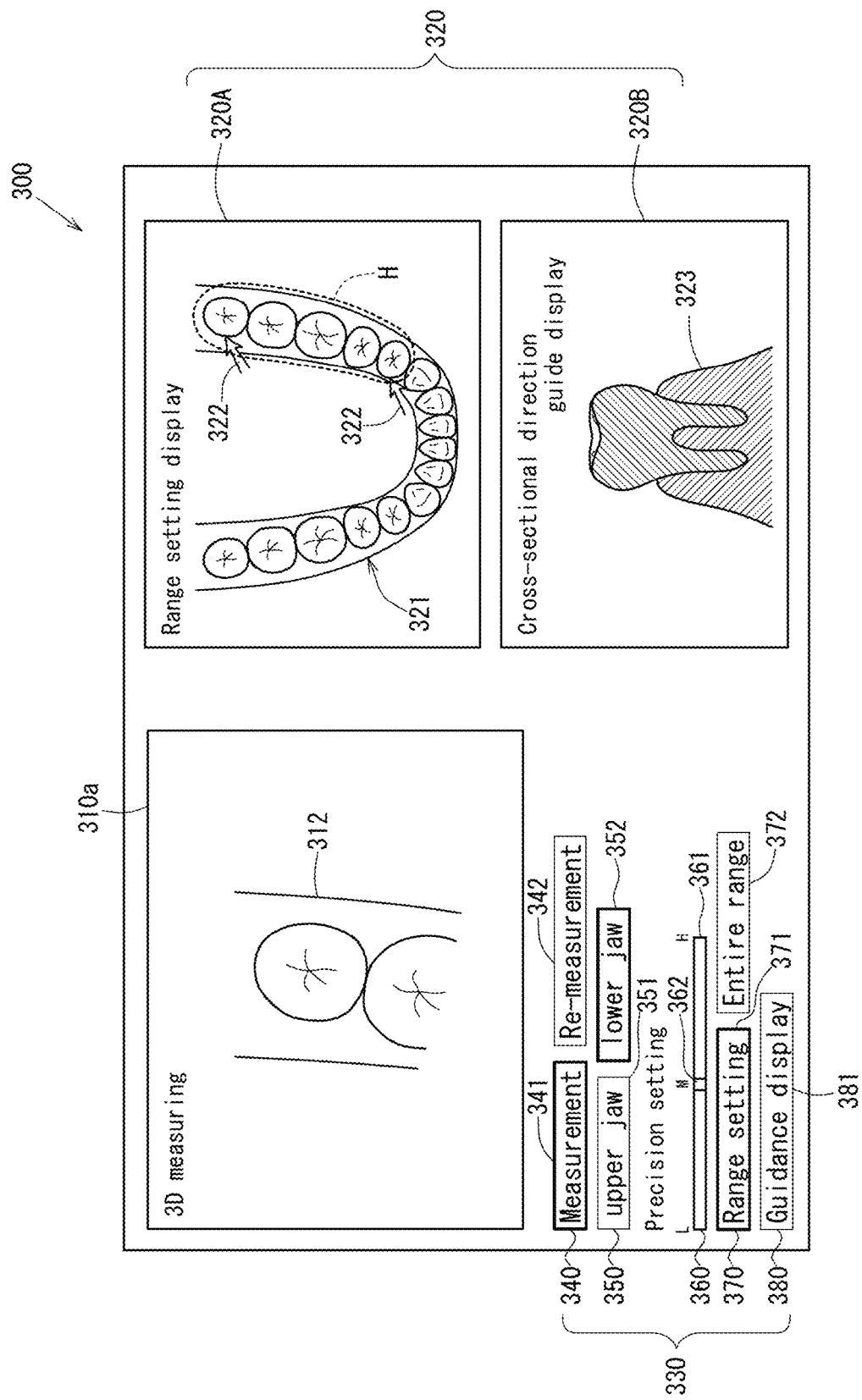
FIG. 8 is a schematic view of the three-dimensional measurement screen.
Figure 9:
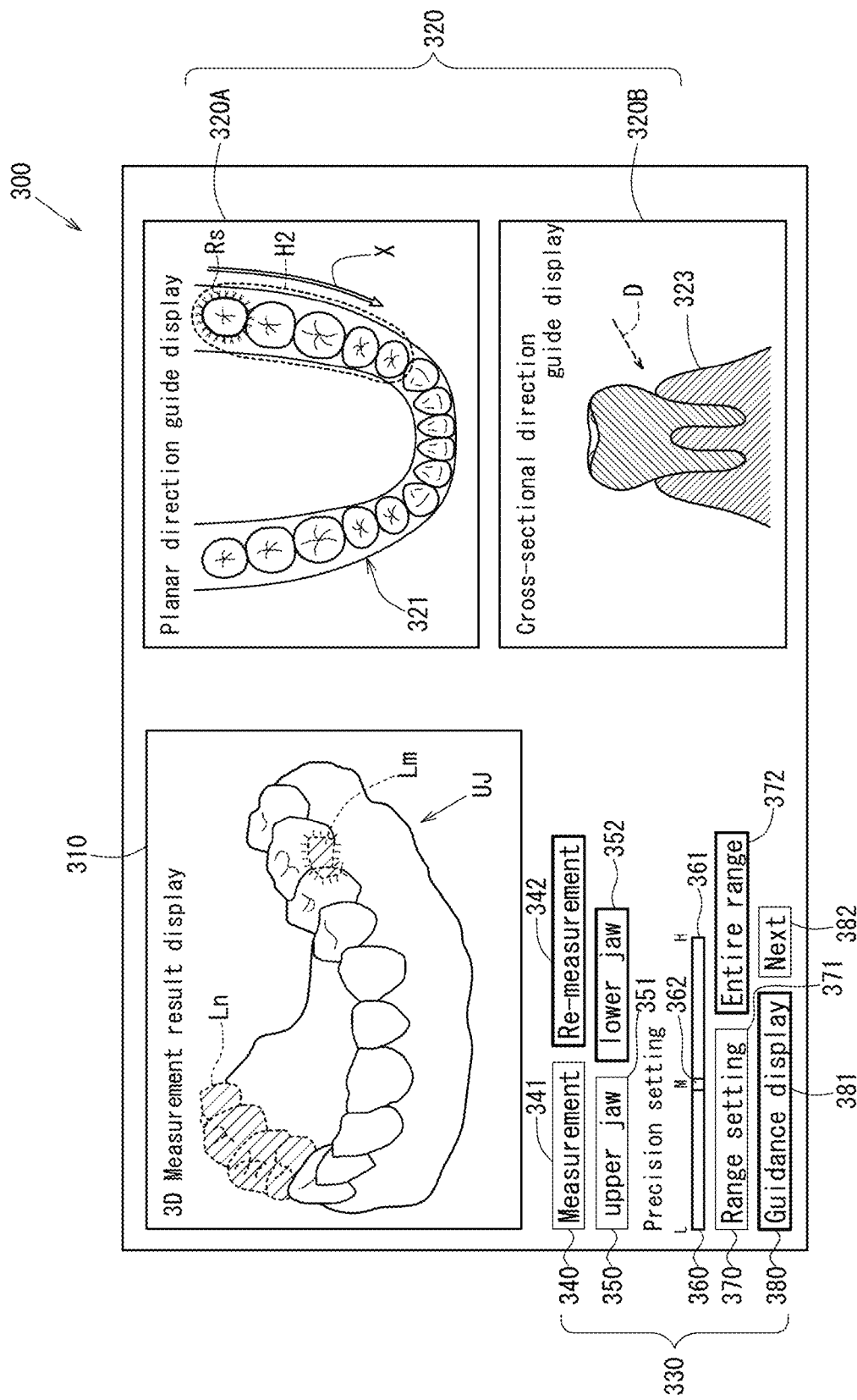
FIG. 9 is a schematic view of the three-dimensional measurement screen.
Figure 10:
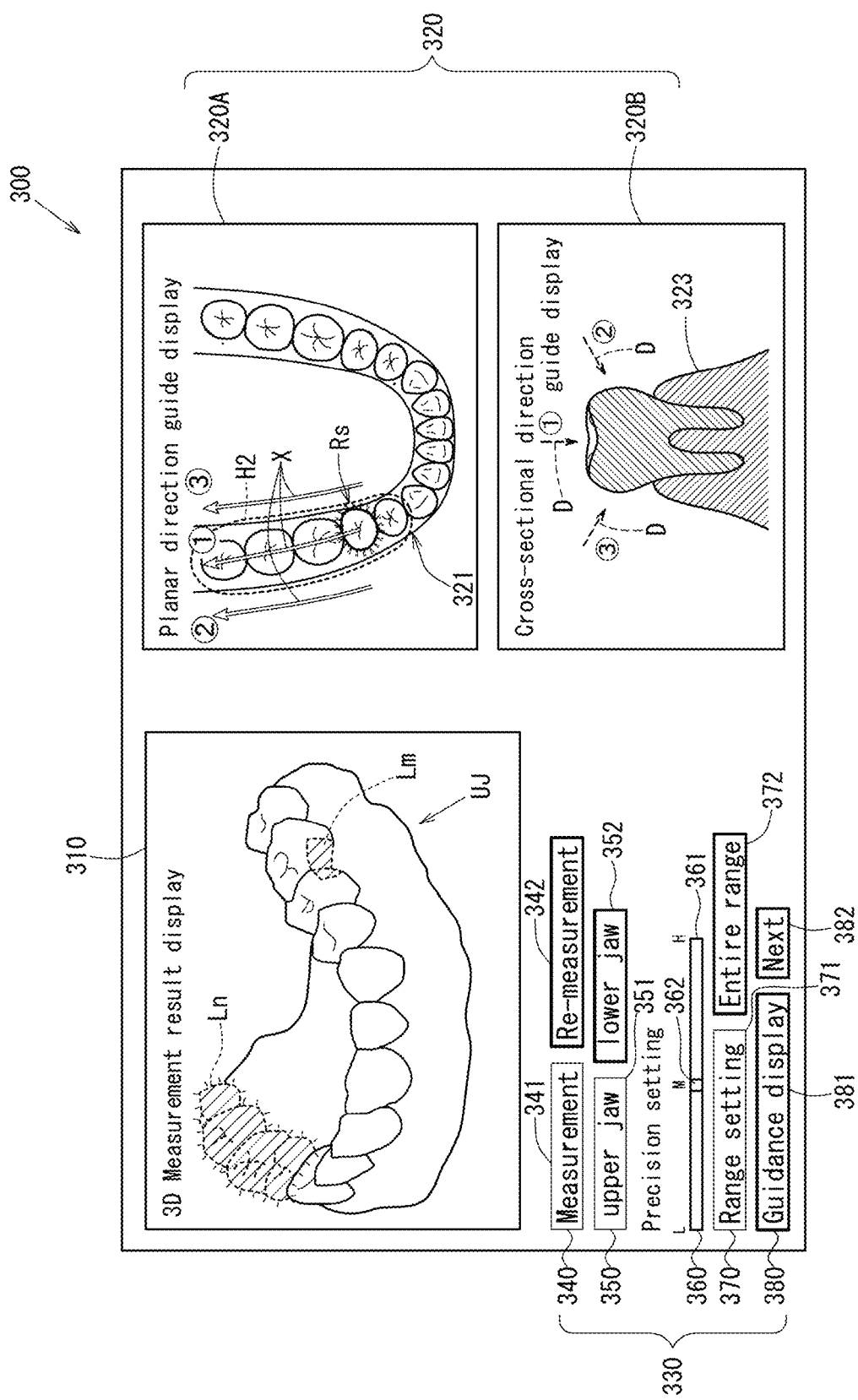
FIG. 10 is a schematic view of the three-dimensional measurement screen.

FIG. 7 through FIG. 10 are each a schematic view of a three-dimensional measurement screen 300. In more detail, FIG. 7 is a schematic view showing elements of the three-dimensional measurement screen 300. FIG. 8 is a schematic view of the three-dimensional measurement screen 300 when a measurement range is to be set. FIG. 9 is a schematic view of the three-dimensional measurement screen 300 when the information partially-lacking site Lm is to be re-measured. FIG. 10 is a schematic view of the three-dimensional measurement screen 300 when the unmeasured site Ln is to be re-measured. FIG. 11 shows a guide display portion in the three-dimensional measurement screen 300 an embodiment other than the embodiment described with reference to FIG. 1 through FIG. 10.

As shown in FIG. 1 and FIG. 2, the three-dimensional measurement system 1 corresponding to a three-dimensional measurement device includes a three-dimensional measurement main body 20 and a scanner 10 connected with the three-dimensional measurement main body 20. The scanner 10 corresponds to a three-dimensional measurement portion. The three-dimensional measurement system 1 scans a desired measurement target site in an oral cavity, for example, the lower jaw UJ or the upper jaw (not shown), to measure a three-dimensional shape of the measurement target site.

As shown in FIG. 3, the scanner 10 includes a generally cylindrical main body 10a and a tip-side insertable portion 10b that is slightly tapered and flattened toward a tip thereof. The tip-side insertable portion 10b has an illumination window 10c formed in a bottom surface of a tip portion thereof. The main body 10a includes an operation button 10d provided on a top surface thereof. The scanner 10 is connected with the three-dimensional measurement main body 20 by a connection cable 10e.

As shown in FIG. 2, the scanner 10 includes a control portion 11, a three-dimensional measurement unit 12, an operation portion 13, and a detection portion 14 built therein.

The three-dimensional measurement unit 12 includes a light emitting portion 121 emitting light to be directed toward the measurement target site through the illumination window 10c and a light receiving portion 122. The emitted light is reflected by the measurement target site and is directed toward, and received by, the light receiving portion 122 through the illumination window 10c as reflected light.

A light guide path (not shown) is provided between the illumination window 10c and the three-dimensional measurement unit 12. The light emitted by the light emitting portion 121 is guided by the light guide path to be directed through the illumination window 10c. The reflected light directed through the illumination window 10c is guided by the light guide path to be received by the light receiving portion 122.

The operation portion 13 acts at least as a measurement operation portion 131 controlling start and finish of the three-dimensional measurement and re-measurement and a measurement range specification operation portion 132 specifying the measurement range H (see FIG. 6(a)). The operation portion 13 is provided as the operation button 10d.

Regarding the scanner 10 including the above-described elements, the three-dimensional measurement unit 12, the operation portion 13 and the detection portion 14 are connected with, and controlled by, the control portion 11.

The scanner 10 has the above-described structure. The tip-side insertable portion 10b of the scanner 10 is inserted into the oral cavity such that the illumination window 10c faces the measurement target site, and the operation button 10d is pressed. As a result, light is emitted by the light emitting portion 121 of the three-dimensional measurement unit 12 and is directed toward the measurement target site through the illumination window 10c. Then, the reflected light directed through the illumination window 10c is received by the light receiving portion 122. In this manner, the measurement target site is scanned.

The control portion 11 is communicably connected with a control portion 21 (described below) of the three-dimensional measurement device main body 20. The control portion 11 is controlled by the control portion 21 to transmit the measurement result to the control portion 21.

As shown in FIG. 1, the three-dimensional measurement device main body 20 is a computer connected with a mouse 20a, a keyboard 20b and a monitor 20c such as a liquid crystal display device or the like. As shown in FIG. 2, the three-dimensional measurement device main body 20, as considered as a functional block, includes the control portion 21 and a storage portion 22 built therein, and is connected with an operation portion 23 and an output portion 24. The storage portion 22, the operation portion 23, the output portion 24, and the control portion 11 of the scanner 10 are connected with, and controlled by, the control portion 21.

The control portion 21 includes a CPU and acts as a computation processing portion 210.

In more detail, the control portion 21 acts as the computation processing portion 210 having functions of a three-dimensional measurement information creation portion 211, a measurement guide creation portion 212, a measurement information-insufficient site detection portion 213, and a setting processing portion 214.

The three-dimensional measurement information creation portion 211 creates three-dimensional measurement information on the measurement target site based on the measurement result provided by the scanner 10 as a result of the scanning.

The measurement guide creation portion 212 acts as a re-measurement start position specification portion 212a, a re-measurement range specification portion 212b, or a re-measurement route and direction specification portion 212c described below, and creates guide information on a re-measurement process including a measurement range, a measurement route, a measurement direction, a measurement speed or the like for the re-measurement.

In more detail, the re-measurement start position specification portion 212a specifies the re-measurement start position Rs (see FIG. 6(c) and FIG. 6(e)) for the re-measurement. The re-measurement range specification portion 212b specifies a measurement range for the re-measurement (hereinafter, referred to as the "re-measurement range H2") and displays the re-measurement range H2 for a dental arch illustration 321 in an articulation direction guide display 320A (see FIG. 7).

The re-measurement route and direction specification portion 212c specifies the measurement route, the measurement direction, and the measurement speed for the re-measurement, and displays guide information such as measurement direction D, measurement route X and the like for the dental arch illustration 321 in the articulation direction guide display 320A (see FIG. 7) or for a cross-sectional illustration 323 in a cross-sectional guide display portion 320B (see FIG. 7).

The measurement information-insufficient site detection portion 213 detects a measurement information-insufficient site for which measurement information is insufficient based on the measurement result provided by the scanner 10.

The setting processing portion 214 sets setting information on measurement conditions such as the measurement range H, a measurement precision and the like described below.

The control portion 21 including the CPU or the like acts as the computation processing portion 210 in cooperation with various programs stored on the storage portion 22 described below.

The storage portion 22 is a storage device including an HDD, an SSD or the like. The storage portion 22 acts as a measurement result storage portion 221, a re-measurement result storage portion 222, a three-dimensional measurement information storage portion 223 and a setting information storage portion 224. The storage portion 22 has, stored thereon, an execution program usable to execute the above-described processes, a control program usable to control various devices connected with the control portion 11, and the like.

The measurement result storage portion 221 has, stored thereon, measurement information acquired from a initial three-dimensional measurement performed by the scanner 10. The re-measurement result storage portion 222 has, stored thereon, measurement information acquired from the re-measurement performed by the scanner 10. The three-dimensional measurement information storage portion 223 has, stored thereon, the three-dimensional measurement information created by the three-dimensional measurement information creation portion 211. The setting information storage portion 224 has, stored thereon, the setting information set by the setting processing portion 214.

The operation portion 23 includes a monitor 231 (20c) acting as a measurement range setting operation portion 231a and a measurement precision setting operation portion 231b, and an input device 232 including the mouse 232a (20a) and the keyboard 232b (20b). As described below, the monitor 231 (20c) acts as the measurement range setting operation portion 231a and the measurement precision setting operation portion 231b in cooperation with the operation button 10d of the scanner 10 that may be pressed to operate a setting operation portion 330 in the three-dimensional measurement screen 300 displayed on the monitor 231, the mouse 20a or the keyboard 20b.

The output portion 24 includes a monitor 241 (20c) acting as a measurement result display unit 24a, a measurement guide portion 24b and a measurement start position notification portion 24c, and also includes a light output portion 242 and an audio signal output portion 243.

As described below, the monitor 241 (20c) acts as the measurement result display unit 24a for a measurement result image display portion 310 in the three-dimensional measurement screen 300 (see FIG. 7) displayed on the monitor 241, and also acts as the measurement guide portion 24b and the measurement start position notification portion 24c for a guide display portion 320 in the three-dimensional measurement screen 300 (see FIG. 7).

In FIG. 2, the light output portion 242 and the audio signal output portion 243 are shown as being included in the output portion 24 and connected with the three-dimensional measurement main body 20. Alternatively, the light output portion 242 and the audio signal output portion 243 may be included in the scanner 10 or included in the three-dimensional measurement main body 20.

With reference to FIG. 5, three-dimensional measurement performed by use of the three-dimensional measurement system 1 having the above-described structure will be described. In the following description with reference to FIG. 5, the measurement target is the entirety of the lower jaw UJ as shown in FIG. 5(a).

For measuring the entirety of the lower jaw UJ, as shown in FIG. 5(b), the tip-side insertable portion 10b of the scanner 10 is inserted into the oral cavity, and the scanner 10 is moved along the dental arch while light emitted by the light emitting portion 121 is directed through the illumination window 10c toward the measurement target site such as teeth T, and gingiva G or the like.

The reflected light from the measurement target site illuminated with the light is directed through the illumination window 10c to be received by the light receiving portion 122. The measurement information acquired by the control portion 11 is transmitted to the control portion 21. Based on the received measurement information, the control portion 21 creates three-dimensional measurement information by the three-dimensional measurement information creation portion 211. As a result, as shown in FIG. 5(d), the three-dimensional measurement image 311 is displayed in the measurement result image display portion 310.

In FIG. 5(c), the unmeasured site Ln is represented with the dashed line for the sake of convenience. For such a portion, no measurement information is acquired, and thus actually, an image of such a portion is not displayed. The three-dimensional measurement information created by the three-dimensional measurement information creation portion 211 and image information on the three-dimensional measurement image 311 are stored on the three-dimensional measurement information storage portion 223 of the storage portion 22, and the measurement information received by the control portion 21 is stored on the measurement result storage portion 221.

In the case where, for example, the scanner 10 is moved up to about half of the dental arch, measurement information on about half of the lower jaw UJ as the measurement target is acquired by the three-dimensional measurement information creation portion 211. Therefore, the three-dimensional measurement information creation portion 211 creates three-dimensional measurement information on about half of the lower jaw UJ on which the measurement information is acquired. As shown in FIG. 5(c), the three-dimensional measurement image 311 on about the half of the lower jaw UJ is displayed in the measurement result image display portion 310. In FIG. 5(c), the unmeasured site Ln is represented with the dashed line for the sake of convenience. In actuality, an image of such a portion is not displayed.

Now, with reference to FIG. 6, measurement information-insufficient site detection of detecting, for example, an unmeasured site Ln and a re-measurement guide in the three-dimensional measurement performed by use of the three-dimensional measurement system 1 will be described. In the following description, made with reference to FIG. 6, on the measurement information-insufficient site detection and the re-measurement guide for the three-dimensional measurement, the measurement target is a part of the lower jaw UJ as shown in FIG. 6(a).

First, the measurement range specification operation portion 132 of the scanner 10 and the measurement range setting operation portion 231a of the operation portion 23 cooperate with each other to specify a part of the lower jaw UJ. When this occurs, the control portion 11 sets the range set by the setting processing portion 214 as the measurement range H, and stores the measurement range H as the setting information on the setting information storage portion 224. The measurement information acquired by the scanner 10 as a result of the scanning on the measurement range H specified in the lower jaw UJ is received by the control portion 21. Based on the received measurement information, the control portion 21 detects a measurement information-insufficient site in measurement information by the measurement information-insufficient site detection portion 213.

The measurement range H may be set after the scanning. In this case, the measurement information-insufficient site varies in accordance with the size of the measurement range H set after the scanning.

This will be described more specifically. In the case where, as shown in FIG. 6(b), a part of the measurement range H is not measured, namely, is unmeasured, the measurement information-insufficient site detection portion 213 detects the unmeasured site Ln in the measurement information on the measurement range H. In this case, in order to re-measure the unmeasured site Ln, the control portion 21 specifies the re-measurement start position Rs by the re-measurement start position specification portion 212a, and also specifies the re-measurement range H2, starting from the re-measurement start position Rs and encompassing the entirety of the unmeasured site Ln, by the re-measurement range specification portion 212b. At this point, the re-measurement route and direction specification portion 212c may specify the measurement direction D or the measurement route X.

Specified as the re-measurement start position Rs is a characteristic site, in the measurement information, that is highly adaptable with the re-measurement information, which corresponds to a re-measurement result. Therefore, as shown in FIG. 6(c), a tooth T that is different from a tooth T adjacent to the unmeasured site Ln but is more highly adaptable with the re-measurement information may be specified as the re-measurement start position Rs. Herein, the "characteristic site that is highly adaptable" is determined based on the number of the characteristic parts or the number of the characteristic sites extracted from the measurement information, which corresponds to a measurement result, the shapes of the characteristic parts that are easily adaptable, the degree of recognition of the characteristic sites or the like.

Another type of measurement information-insufficient site is the information partially-lacking site Lm. In the case where the entirety of the measurement range H is measured based on the measurement information but a part thereof is lacking information, the measurement information-insufficient site detection portion 213 detects such a part in the measurement range H as the information partially-lacking site Lm.

In this case, in order to re-measure the information partially-lacking site Lm, the control portion 21 specifies the re-measurement start position Rs by the re-measurement start position specification portion 212a, and also specifies the re-measurement range H2, starting from the re-measurement start position Rs and encompassing the information partially-lacking site Lm, by the re-measurement range specification portion 212b.

As shown in FIG. 6(e), the re-measurement range H2 may be a range starting from the re-measurement start position Rs and encompassing the information partially-lacking site Lm. Alternatively, a range encompassing the tooth T exceeding the information partially-lacking site Lm may be specified as the re-measurement range H2. This is for the purpose of allowing the three-dimensional measurement information creation portion 211 to synthesize the measurement information and the re-measurement information with high precision so as to create the three-dimensional measurement information.

As described above, the measurement information-insufficient site to be detected by the measurement information-insufficient site detection portion 213 may be the unmeasured site Ln, the information partially-lacking site Lm or a measurement precision-insufficient site for which the set measurement precision is not satisfied.

Now, the three-dimensional measurement screen 300 to be displayed on the monitor 20c at the time of the three-dimensional measurement performed by the three-dimensional measurement system 1 having the above-described structure will be described.

The three-dimensional measurement screen 300 includes the measurement result image display portion 310 provided in a top left area, the display portion 320 provided in a right area, and the setting operation portion 330 provided in a bottom left area.

The measurement result image display portion 310, which corresponds to a measurement result display portion, displays an image of the three-dimensional measurement information created by the three-dimensional measurement information creation portion 211 (hereinafter, such an image will be referred to as the three-dimensional measurement image 311). As shown in FIG. 8, the measurement result image display portion 310 also acts as a measurement state display portion 310a displaying an image of a measurement state at the time of measurement (hereinafter, such an image will be referred to as a "measurement state image 312").

The guide display portion 320, which correspond to a re-measurement start position notification portion and a re-measurement process guide portion, includes the articulation direction guide display 320A provided in a top right area and the cross-sectional guide display portion 320B provided in a bottom right area. The guide display portion 320 is used to provide a guide display for the measurement or to set the measurement range.

Therefore, the articulation direction guide display 320A displays the dental arch illustration 321 in an articulation direction (hereinafter, referred to as the "dental arch illustration 321") of either the upper jaw or the lower jaw selected by a measurement target jaw selection portion 350 described below. The articulation direction guide display 320A may also display a cursor 322 usable to set a measurement range for the dental arch illustration 321, the measurement range H, the re-measurement range H2, the re-measurement start position Rs, the measurement route X and the like. In FIG. 7 through FIG. 10, the dental arch illustration 321 of the lower law is displayed in the articulation direction guide display 320A.

The cross-sectional guide display portion 320B displays the illustration 323 in a cross-sectional direction of the tooth T in the measurement range H in the upper jaw or the lower jaw that is selected (hereinafter, such an illustration will be referred to as the "cross-sectional illustration 323"). The cross-sectional guide display portion 320B may also display the measurement direction D for the cross-sectional illustration 323. In FIG. 7 through FIG. 10, the cross-sectional illustration 323 of the lower law is displayed in the cross-sectional guide display portion 320B.

The setting operation portion 330 provided in a bottom left area of the three-dimensional measurement screen 300 includes a measurement selection portion 340, the measurement target jaw selection portion 350, a measurement precision setting portion 360, a measurement range setting portion 370, and a guide display operation button 380 in this order from the top.

The measurement selection portion 340 includes a measurement button 341 that is pressed in the case where the scanning to be performed is an initial three-dimensional measurement, and a re-measurement button 342 that is pressed in the case where the scanning to be performed is a re-measurement.

The measurement target jaw selection portion 350 includes an upper jaw button 351 that is pressed in the case where the measurement target is the upper jaw, and a lower jaw button 352 that is pressed in the case where the measurement target is the lower jaw.

The measurement precision setting portion (the precision setting portion) 360 displays a scroll bar 361 usable to set the measurement precision for the three-dimensional measurement on the measurement range H. A scroll button 362 is moved leftward or rightward along the scroll bar 361 by use of the input device 232 or the operation button 10d, so that the measurement range is set. In this embodiment, as the scroll button 362 is moved rightward, the measurement precision is increased, whereas as the scroll button 362 is moved leftward, the measurement precision is decreased. The scroll button 362 is set at the center of the scroll bar 361 as default. The measurement precision may be partially variable within the measurement range H.

The measurement range setting portion 370 includes a range setting button 371 usable to set an optional range as the measurement range H and an entire range button 372 usable to set the entirety of the dental arch has the measurement range H.

The guide display operation button 380 is pressed in order to provide a guide display (Rs, X, H2, D) in the guide display portion 320. As described below, in the case where there are multiple measurement information-insufficient sites, a next button 382 is displayed, so that a guide display for re-measurement on another measurement information-insufficient site is provided (see FIG. 9 and FIG. 10).

Now, with reference to the flowchart shown in FIG. 4, a measurement method for performing three-dimensional measurement on the lower jaw UJ by use of the three-dimensional measurement system 1 including the monitor 20c displaying the three-dimensional measurement screen 300 will be described.

For the three-dimensional measurement, as shown in FIG. 8, the range setting button 371 acting as the measurement range setting operation portion 231a is pressed by the operation button 10d acting as the measurement range specification operation portion 132 or the input device 232. In the case where a measurement range in the lower jaw UJ is set by the cursor 322 for the dental arch illustration 321 displayed in the articulation direction guide display 320A (step s1: Yes), the setting processing portion 214 sets the specified range as the measurement range H and stores the measurement range H on the setting information storage portion 224 (step s2; measurement range setting process, which corresponds to a measurement range setting step).

By contrast, in the case where, at the time of the three-dimensional measurement, the entire range button 372 acting as the measurement range setting operation portion 231a is pressed by the operation button 10d acting as the measurement range specification operation portion 132 or the input device 232 (step s1: No), the setting processing portion 214 sets the entirety of the lower jaw UJ as the measurement range H.

In the case where the scroll button 362 in the measurement precision setting portion 360 acting as the measurement precision setting operation portion 231b is moved leftward or rightward by the operation button 10d or the input device 232 (step s3: Yes), the setting processing portion 214 sets the specified measurement precision and stores the specified measurement precision on the setting information storage portion 224 (step s4; measurement precision setting process, which corresponds to a measurement precision setting step).

By contrast, in the case where the measurement precision setting portion 360 acting as the measurement precision setting operation portion 231b is not pressed (step s3: No), the setting processing portion 214 sets the default measurement precision.

After the measurement conditions are set in this manner, the measurement button 341 is pressed by the input device 232. The tip-side insertable portion 10b is inserted into the oral cavity such that the illumination window 10c faces the teeth T or the gingiva G in the measurement range H, and the operation button 10d acting as the measurement operation portion 131 is pressed. Thus, the three-dimensional measurement is started (step s5).

In step S5, the control portion 11 controls the light emission portion 121 to emit light. The light emitted by the light emission portion 121 is guided along the above-described light guide path to be directed through the illumination window 10c toward the teeth T or the gingiva G in the measurement range H. The light reflected by the teeth T or the gingiva G is directed through the illumination window 10c to enter the inside of the scanner 10 and is guided along the light guide path to be received by the light receiving portion 122.

The information on the reflected light that is received by the light receiving portion 122 is transmitted to the control portion 21 via the control portion 11 as the measurement information. Based on the received measurement information, the control portion 21 displays the measurement state image 312 in the measurement state display portion 310a as shown in FIG. 8, and stores the received measurement information on the measurement result storage portion 221 (step s5A; measurement information acquisition process).

Such three-dimensional measurement is continued until the operation button 10d acting as the measurement operation portion 131 is pressed again. When the operation button 10d is pressed to finish the three-dimensional measurement, the control portion 11 detects the measurement information-insufficient site (Lm, Ln) from the received measurement information (step s6; measurement information-insufficient site detection process).

In the measurement information-insufficient site detection process (step s6), as described above, the measurement information-insufficient site detection portion 213 performs an unmeasured site detection process (step s6A) of detecting the unmeasured site Ln from the received measurement information, an information partially-lacking site detection process (step s6B) of detecting the information partially-lacking site from the received measurement information, or a measurement precision insufficiency detection process (step s6C) of detecting a measurement precision-insufficient site for which the set measurement precision is not satisfied from the received measurement information.

Now, it is assumed that as a result of the unmeasured site detection process (step s6A), the information partially-lacking site detection process (step s6B) or the measurement precision insufficiency detection process (step s6C) being performed in the measurement information-insufficient site detection process (step s6), the measurement information-insufficient site such as the information partially-lacking site Lm, the unmeasured site Ln, the measurement precision-insufficient site or the like is not detected (step s7: No). In this case, based on the received measurement information, the control portion 21 creates the three-dimensional measurement information by the three-dimensional measurement information creation portion 211, and stores the three-dimensional measurement information on the three-dimensional measurement information storage portion 223. The control portion 21 also displays the three-dimensional measurement information as the three-dimensional measurement image 311 in the measurement result image display portion 310 (step s8; three-dimensional measurement information creation process, which corresponds to a three-dimensional measurement information creation step).

By contrast, in the case where, as a result of the measurement information-insufficient site detection process (step s6), the measurement information-insufficient site is detected (step s7: Yes), the control portion 21 performs a re-measurement guide specification and display process by the measurement guide creation portion 212 (step s9). The re-measurement guide specification and display process is to set a guide display such as the re-measurement start position Rs, the measurement range H, the measurement route X, the measurement direction D, or the like.

In the following description, it is assumed that two measurement information-insufficient sites, namely, the information partially-lacking site Lm and the unmeasured site Ln, are detected in the measurement information-insufficient site detection process (step s6). More specifically, with reference to FIG. 9, the guide display provided in the case where the information partially-lacking site Lm is detected in a cheek-side part of the teeth T on the right side will be described. With reference to FIG. 10, the guide display provided in the case where the unmeasured site Ln is detected in left back teeth T will be described.

In the re-measurement guide specification and display process (step s9), which corresponds to a re-measurement process guide step, the control portion 21 performs a re-measurement start position specification and display process (step s9A; corresponding to a re-measurement start position notification step), a re-measurement range specification and display process (step s9B), a re-measurement route specification and display process (step s9C), a re-measurement direction specification and display process (step s9D), and a re-measurement speed specification and display process (step s9E). In the re-measurement start position specification and display process (step s9A) performed by the re-measurement start position specification portion 212a, a characteristic site extraction process of extracting a characteristic site from the received measurement information is performed and the re-measurement start position Rs for the re-measurement is specified. In the re-measurement range specification and display process (step s9B) performed by the re-measurement range specification portion 212b, the re-measurement range H2 is specified. In the re-measurement route specification and display process (step s9C) performed by the re-measurement route and direction specification portion 212c, the measurement route for the re-measurement is specified. In the re-measurement direction specification and display process (step s9D) performed by the re-measurement route and direction specification portion 212c, the measurement direction for the re-measurement is specified. In the re-measurement speed specification and display process (step s9E), the measurement speed for the re-measurement is specified. The control portion 21 displays the re-measurement start position Rs, the re-measurement range H2, and the measurement route X for the dental arch illustration 321 in the articulation direction guide display 320A in the three-dimensional measurement screen 300, and displays the measurement direction D for the cross-sectional illustration 323 in the cross-sectional guide display portion 320B.

It is assumed that, for example, as shown in FIG. 9, the information partially-lacking site Lm is detected in a part of the second and third teeth T from the back on the right side. In this case, the first teeth T from the back on the right side is displayed as the re-measurement start position Rs, and a range encompassing four teeth T from the re-measurement start position Rs toward the front center (front side) of the dental arch is set and displayed as the re-measurement range H2.

In addition, the measurement route X representing the direction from the back toward the front center (front side) is displayed as a guide display for the dental arch illustration 321 in the articulation direction guide display 320A. The measurement direction D as the direction for the re-measurement performed along the measurement route X is displayed for the cross-sectional illustration 323 in the cross-sectional guide display portion 320B.

Now, in the case where as shown in FIG. 10, the unmeasured site Ln is detected in the four teeth T in the back on the left side, the next button 382 is pressed in the state where the guide display on the information partially-lacking site Lm is provided in the three-dimensional measurement screen 300 as shown in FIG. 9. Thus, the above-described state in FIG. 9 is transferred to the state shown in FIG. 10, in which the guide display is provided for the unmeasured site Ln.

In this case, the unmeasured site Ln is detected in the four back teeth on the left side, and thus, measurement is to be performed in the articulation direction and also from the cheek side and the tongue side, in which measurement is difficult. Therefore, three measurement routes X are provided for the dental arch illustration 321 in the articulation direction guide display 320A, and also three measurement directions D are provided for the cross-sectional illustration 323 in the cross-sectional guide display portion 320B. In addition, numbers are displayed to represent the order of measurement for the measurement routes X and the measurement directions D.

In this manner, in the re-measurement guide specification and display process (step s9), the re-measurement start position Rs, the re-measurement range H2 and the measurement routes X are provided as guide displays for the dental arch illustration 321 in the articulation direction guide display 320A, and the measurement directions D are provided as guide displays for the cross-sectional illustration 323 in the cross-sectional guide display portion 320B. In this state, the re-measurement button 342 is pressed by the input device 232. The tip-side insertable portion 10b is inserted into the oral cavity such that the illumination window 10c faces the teeth T and the gingiva G in the re-measurement range H2, and the operation button 10d acting as the measurement operation portion 131 is pressed. As a result, the re-measurement is started (step s10).

In step s10, like in the measurement information acquisition process (step s5A), light is directed toward the teeth T and the gingiva G in the re-measurement range H2. The reflected light is received by the light receiving portion 122, and the information on the received light is transmitted to the control portion 21 via the control portion 11. The control portion 21 stores the received re-measurement information on the re-measurement result storage portion 222 (step s10A; re-measurement information acquisition process).

Then, the procedure of the three-dimensional measurement method returns to step s6, where the measurement information-insufficient site detection process of detecting the measurement information-insufficient sites (Lm, Ln) is performed on the re-measurement information received by the light receiving portion 122. In the case where no measurement information-insufficient sites is detected in the re-measurement information, the control portion 21 creates the three-dimensional measurement information by the three-dimensional measurement information creation portion 211 based on the measurement information stored on the measurement result storage portion 221 and the received re-measurement information. The control portion 21 stores the three-dimensional measurement information on the three-dimensional measurement information storage portion 223. The control portion 21 also displays the three-dimensional measurement information as the three-dimensional measurement image 311 in the measurement result image display portion 310 (step s8; three-dimensional measurement information creation process).

By contrast, in the case where the measurement information-insufficient site is detected in the re-measurement information, the procedure advances to steps s9 and s10, where the control portion 21 performs the re-measurement again. This is repeated until no measurement information-insufficient site is detected in the measurement information-insufficient site detection process (step s6).

As described above, the three-dimensional measurement method is performed by use of the three-dimensional measurement system 1. The three-dimensional measurement system 1 includes the scanner 10 performing three-dimensional measurement on the measurement range H; the measurement information-insufficient site detection portion 213 detecting the measurement information-insufficient sites Lm and Ln for which the measurement information acquired by the scanner 10 is insufficient; the guide display portion 320 displaying the re-measurement start position Rs at which the re-measurement on the information-insufficient sites Lm and Ln detected by the measurement information-insufficient site detection portion 213 is to be started; and the three-dimensional measurement information creation portion 211 adapting a characteristic site having characteristic information in the re-measurement information acquired by the re-measurement performed by the scanner 10 on an area starting from the re-measurement start position Rs and encompassing the measurement information-insufficient sites Lm and Ln to a characteristic site having characteristic information in the measurement information on a measured area, to create the three-dimensional measurement information on the measurement range H. The three-dimensional measurement method includes the three-dimensional measurement step (step s5) of performing the three-dimensional measurement on the measurement range H; the measurement information-insufficient site detection process (step s6) of detecting the measurement information-insufficient sites Lm and Ln for which the measurement information acquired in the three-dimensional measurement step (step s6) is insufficient; the re-measurement start position specification and display process (step s9A) of displaying the re-measurement start position Rs at which the re-measurement on the measurement information-insufficient sites Lm and Ln detected by the measurement information-insufficient site detection process (step s6); the re-measurement step (step s10) of re-measuring an area starting from the re-measurement start position Rs and encompassing the measurement information-insufficient sites Lm and Ln; and the three-dimensional measurement information creation process (step s8) of adapting a characteristic site having characteristic information in the re-measurement information acquired in the re-measurement step (step s10) to a characteristic site having characteristic information in the measurement information acquired in the three-dimensional measurement step (step s5), to create the three-dimensional measurement information on the measurement range H. Thus, the data amount and the processing load are prevented from increasing, and the measurement information with high precision is provided.

This will be described in more detail. The re-measurement start position Rs, at which the re-measurement on the measurement information-insufficient sites Lm and Ln is to be started, is displayed on the guide display portion 320. The measurement information-insufficient sites Lm and Ln are sites for which the measurement information acquired in the three-dimensional measurement step (step s5) is insufficient. Because of the display, the re-measurement is performed on an area starting from the displayed re-measurement start position Rs and encompassing the measurement information-insufficient sites Lm and Ln. Thus, the measurement information-insufficient sites Lm and Ln are re-measured with certainty.

According to an embodiment of the present invention, the measurement information-insufficient sites Lm and Ln are displayed as a three-dimensional image. In such a display, the shapes of the measurement-insufficient sites are estimated from the measured site and displayed. In addition, in order to re-measure the measurement information-insufficient sites Lm and Ln quickly, the direction, the position and the range of scanning for the re-measurement are also displayed.

A characteristic site having characteristic information in the re-measurement information acquired in step s10 and a characteristic site having characteristic information in the measurement information acquired in the three-dimensional measurement step (step s5) are adapted to each other to create the three-dimensional measurement information on the measurement range H. Therefore, the three-dimensional measurement information on the measurement range H is created with high precision based on the re-measurement information and the measurement in acquired in the three-dimensional measurement step (step s5).

In the re-measurement start position specification and display step (step s9A), a highly adaptable characteristic site is detected based on the measurement information acquired in the three-dimensional measurement step (step s5) and is specified as the re-measurement start position Rs. Therefore, the three-dimensional measurement information is created with higher precision.

This will be described in more detail. A highly adaptable characteristic site is specified as the re-measurement start position Rs. Therefore, the re-measurement information and the measurement information acquired in the three-dimensional measurement step (step s5) are synthesized with each other based on the highly adaptable characteristic site specified as the re-measurement start position Rs. Thus, the three-dimensional measurement information is created with high precision.

In the measurement precision setting step (step s4), a setting of the measurement precision is accepted. In the measurement information-insufficient site detection process (step s6), insufficiency of the measurement information, acquired in the three-dimensional measurement step (step s5), on the corresponding site is detected based on the set measurement information. Therefore, the three-dimensional measurement information of a desired precision is created. In more detail, in the case where a certain site in the measurement range H has already been measured but the desired measurement precision is not satisfied for the site, the site is re-measured. Therefore, the three-dimensional measurement information of a desired precision is created.

In the case where the measurement precision for a treatment target site in the measurement range H is set to be higher than that of another site, as compared with the case where the measurement precision for the entirety of the measurement range H is set to be high, the data amount is decreased and the processing load is suppressed from increasing.

In the re-measurement guide specification and display process (step s9), the re-measurement process in the re-measurement step (step s10) is provided by a guide display such as the measurement direction D, the measurement route X or the like. Therefore, the re-measurement is performed more accurately with no waste. As compared with the case where, for example, the re-measurement is performed with a wasteful route, the measurement is performed more accurately and more efficiently while the data amount is decreased and the processing load is suppressed from increasing.

The setting of the measurement range H in the oral cavity is accepted. Therefore, the measurement is performed only on the desired measurement range H. Thus, the measurement is performed more accurately and more efficiently while the data amount is decreased and the processing load is suppressed from increasing.

The insufficient site detection step according to an embodiment of the present invention corresponds to the measurement information-insufficient site detection process (step s6) in the above-described embodiment; and similarly, the re-measurement start position notification step corresponds to the re-measurement start position specification and display process (step s9A);

the re-measurement result corresponds to the re-measurement information;

the measurement result corresponds to the measurement information;

the three-dimensional measurement information creation step corresponds to the three-dimensional measurement information creation process (step s8);

the measurement precision setting step corresponds to the measurement precision setting process (step s4);

the re-measurement process guide step corresponds to the re-measurement guide specification and display process (step s9);

the measurement range setting step corresponds to the measurement range setting process (step s2);

the three-dimensional measurement device corresponds to the three-dimensional measurement system 1;

the three-dimensional measurement portion corresponds to the scanner 10;

the insufficient site detection portion corresponds to the measurement information-insufficient site detection portion 213;

the re-measurement start position notification portion corresponds to the guide display portion 320;

the re-measurement process guide portion corresponds to the guide display portion 320; and the measurement result display portion corresponds to the measurement result image display portion 310.

However, the present invention is not limited to the above-described embodiment, and may be carried out in any of many embodiments.

For example, in the above description, the re-measurement start position Rs is specified by the re-measurement start position specification portion 212a. Alternatively, the re-measurement start position Rs may be specified by an operator by use of the operation button 10d acting as the re-measurement start position specification portion or the input device 232. In this case, the re-measurement is started from a position where the re-measurement is easily started. Thus, the re-measurement is performed smoothly.

In the above description, the cursor 322 is operated to specify the measurement range H. Alternatively, a range that is not set as the measurement range H may be specified by the cursor 322, so that such a range that is not specified may be specified as the measurement range H.

As represented with the dashed line in FIG. 2, the scanner 10 may include the detection portion 14 acting at least as a posture detection portion 141 detecting the posture of the scanner 10 and a movement speed detection portion 142 detecting the movement speed of the scanner 10. With such a structure, the movement posture or the movement speed of the scanner 10 during the measurement is detected.

With this structure, as shown in FIG. 11, the tip-side insertable portion 10b of the scanner 10 is drawn as an illustration for the dental arch illustration 321 or the cross-sectional illustration 323 in the guide display portion 320. The illustrated tip-side insertable portion 10b is used to show the measurement routes X or the measurement directions D. In addition, an appropriate measurement route Xa or an appropriate measurement direction Da is displayed while the posture or the movement speed of the scanner 10 is detected by the detection portion 14 as described above.

In the case where the movement speed of the scanner 10 is detected by the detection portion 14, a speed guide Y guiding the movement speed of the scanner 10 may be displayed for the dental arch illustration 321 as a guide display. In this case, for increasing the movement speed, the length or the size of the arrow may be increased, or alternatively, such an increase may be notified by an alarm sound or a voice. For decreasing the movement speed, the length or the size of the arrow may be decreased, or alternatively, such a decrease may be notified by an alarm sound or a voice.

The re-measurement start position Rs may be notified by, for example, a voice or an audio signal provided by the audio signal output portion 243, light emission or a light emission pattern provided by the optical output portion 242, a driving manner different from driving such as vibration of the main body 10a or the like.

In the above description, the measurement information-insufficient site is the unmeasured site Ln, the information partially-lacking site Lm, which is a part lacking measurement information, or the measurement precision-insufficient site for which the set measurement precision is not satisfied. Alternatively, for example, partial lack of the measurement information and insufficiency of the measurement precision may be combined with each other to detect the measurement information-insufficient site.

In a dental care such as a prosthetic treatment of implanting a prosthesis such as a false tooth, a dental crown, a dental bridge or the like in a part of the oral cavity in which a tooth or teeth are lost, an implant treatment, production of a denture, orthodontics or the like, a three-dimensional shape of the site as a target of dental care, as well as an area around the site and an area biting together with the site, is to be grasped accurately.

As a result of the recent development in the dental technology and the measurement technology, a three-dimensional measurement device that scans a desired site in the oral cavity to measure a three-dimensional shape (cubic shape) is used.

With the measurement of a three-dimensional shape performed by use of such a three-dimensional measurement device, the precision of the measurement result varies, more specifically, a highly precise three-dimensional measurement result may not be obtained, in accordance with the measurement skill of the operator or the manner of measurement. For example, Japanese PCT National-Phase Patent Laid-Open Publication No. 2008-537494 proposes a measurement system that guides the order or the direction of scanning for a measurement target site.

Especially, the measurement system described in Japanese PCT National-Phase Patent Laid-Open Publication No. 2008-537494 allows the measurement to be performed easily by performing scanning along with the guide. However, the teeth or the lost part of the teeth as the measurement target has a three-dimensional shape, and therefore, a part thereof cannot be measured by scanning performed in one direction. The teeth as the measurement target may need to be scanned in, for example, multiple directions.

In such a case, the teeth in the measurement range encompassing a desired measurement target site may be scanned one by one in multiple directions, so that a more precise measurement result is provided. However, the scanning is time-consuming and the load on the patient is increased. For this reason, in practice, the measurement range encompassing the measurement target site is scanned in multiple directions.

However, in the case where a large portion of the measurement range can be measured by scanning performed in one direction, namely, in the case where the measurement on only a part of the measurement range is insufficient, scanning on the entirety of the measurement range in multiple directions may undesirably increase the data amount included in the measurement result and increase the processing load of a computation process or the like.

By contrast, in the case where only a measurement-insufficient site is re-scanned, the increase in the data amount and the processing load is prevented. However, in this case, the precision of synthesizing the measurement result of scanning performed for the first time (hereinafter, such a measurement result will be referred to as an "initial measurement result") and the measurement result of the re-scanning performed on only the measurement-insufficient site (hereinafter, referred to as a "re-measurement result"), namely, the precision of synthesizing the re-measurement result to the initial measurement result, is decreased. As a result, it is difficult to provide a highly precise measurement result.

A three-dimensional measurement method and a three-dimensional measurement device according to embodiments of the present invention prevent increase in a data amount and a processing load and provide a highly precise measurement result.

A three-dimensional measurement method for performing three-dimensional measurement on a desired measurement range in an oral cavity according to an embodiment of the present invention includes performing the three-dimensional measurement on the measurement range; detecting a measurement information-insufficient site for which measurement information is insufficient in a measurement result acquired in the three-dimensional measurement; notifying a re-measurement start position at which re-measurement on the measurement information-insufficient site detected in the insufficient site detection is to be started; re-measuring an area starting from the re-measurement start position and encompassing the measurement information-insufficient site; and adapting at least one characteristic site having characteristic information in a re-measurement result acquired by the re-measurement performed in the re-measurement, and at least one characteristic site having characteristic information in the measurement result acquired in the three-dimensional measurement, to each other to create three-dimensional measurement information on the measurement range.

A three-dimensional measurement device for performing three-dimensional measurement on a desired measurement range in an oral cavity according to another embodiment of the present invention includes a three-dimensional measurement portion performing the three-dimensional measurement on the measurement range; an insufficient site detection portion detecting a measurement information-insufficient site for which measurement information is insufficient in a measurement result acquired by the three-dimensional measurement portion; a re-measurement start position notification portion notifying a re-measurement start position at which re-measurement on the measurement information-insufficient site detected by the insufficient site detection portion is to be started; and a three-dimensional measurement information creation portion adapting a characteristic site having characteristic information in a re-measurement result provided by the re-measurement performed by the three-dimensional measurement portion on an area starting from the re-measurement start position and encompassing the measurement information-insufficient site, and a characteristic site having characteristic information in the measurement result provided by the three-dimensional measurement portion, to create three-dimensional measurement information on the measurement range.

The "measurement information-insufficient site for which measurement information is insufficient" may be an unmeasured site that has not been measured in the measurement range, an information partially-lacking site that has been measured but partially lacks measurement information, a measured site for which a desired measurement precision is not satisfied, or a combination thereof.

The "measurement range" may be either of, or both of, the upper jaw and the lower jaw, or the entirety of, or a part of, the dental arch. The "re-measurement start position" may be a tooth, a part of a tooth, a characteristic gingiva, or the like.

The expression "adapt a characteristic site having characteristic information" encompasses, for example, adaptation by image recognition, and also adaptation based on a technology of automatic recognition on an extracted site. In addition to determining whether the characteristic sites are adaptable or not, a process of matching the size or the direction of the adaptable information may be performed. The three-dimensional measurement information encompasses numerical data on the measurement result, and also image data formed based on the numerical data.

The "notification of the re-measurement start position" encompasses, for example, notification by display of an image on a display portion such as a monitor or the like, notification by a voice or a sound, notification by light emission by a light emitting material or a light emitting pattern, and notification by a driving manner different from driving such as vibration or the like.

With the above-described embodiment of the present invention, increase in a data amount and a processing load is prevented, and a highly precise measurement result is provided.

This will be described in more detail. The re-measurement start position, at which the re-measurement on the measurement information-insufficient sites, is to be started is, notified. The measurement information-insufficient sites are sites for which the measurement information is insufficient in the measurement result acquired in the three-dimensional measurement step. Because of the notification, re-measurement is performed on an area starting from the notified re-measurement start position and encompassing the measurement information-insufficient sites. Thus, the area encompassing the measurement information-insufficient sites is re-measured with certainty.

A characteristic site having characteristic information in the re-measurement result acquired by the re-measurement, and a characteristic site having characteristic information in the measurement result acquired by the measurement, are adapted to each other to create three-dimensional measurement information on the measurement range. Therefore, the three-dimensional measurement information on the measurement range is created with high precision based on the re-measurement result and the measurement result.

In an embodiment of the invention, the three-dimensional measurement method may further include detecting a highly adaptable characteristic site among the at least one characteristic site based on the measurement result acquired in the three-dimensional measurement and specifying the highly adaptable characteristic site as the re-measurement start position.

The "highly adaptable characteristic site" will be described. Characteristic sites of a target site are extracted. Whether a certain characteristic site is highly adaptable or not is determined based on the number of characteristic parts of the characteristic sites, the number of the characteristic sites, the shapes of the characteristic parts that are easily adaptable, the degree of recognition of the characteristic sites, or the like.

With the above-described embodiment of the present invention, the three-dimensional measurement information with higher precision is created. This will be described in more detail. A highly adaptable characteristic site is specified as the re-measurement start position. Therefore, the re-measurement result and the measurement result are synthesized with each other based on the highly adaptable characteristic site specified as the re-measurement start position. Thus, the three-dimensional measurement information with high precision is created.

In an embodiment of the invention, the three-dimensional measurement method may further include accepting a specification operation to specify the re-measurement start position. With the above-described embodiment of the present invention, the operator may start the re-measurement from a position where the re-measurement is easily started. Thus, the re-measurement is performed smoothly.

In an embodiment of the invention, the three-dimensional measurement method may further include accepting a setting of a measurement precision for the measurement range. The insufficient site detection may include detecting insufficiency of the measurement information, on a corresponding site, in the measurement result acquired in the three-dimensional measurement based on the measurement precision.

The measurement precision for the measurement range may be set by the number of measurement points per unit area, dpi of a displayed image or the like. The measurement precision may be set for the entirety of the measurement range or for a part of the measurement range.

With the above-described embodiment of the present invention, the three-dimensional measurement information of a desired precision is created. This will be described in more detail. In the case where a certain site in the measurement range has already been measured but the desired measurement precision is not satisfied for the side, the site is re-measured. Therefore, the three-dimensional measurement information of a desired precision is created.

In the case where the measurement precision for a treatment target site in the measurement range is set to be higher than that of another site, as compared with the case where the measurement precision for the entirety of the measurement range is set to be high, the data amount is decreased and the processing load is suppressed from increasing.

In an embodiment of the present invention, the three-dimensional measurement method may further include guiding a re-measurement process in the re-measurement. The re-measurement process may use either one of the measurement location, the measurement direction, the measurement speed and the measurement route for the re-measurement, or a combination thereof.

With the above-described embodiment of the present invention, the re-measurement is performed more accurately with no waste. As compared with the case where, for example, the re-measurement is performed with a wasteful route, the measurement is performed more accurately and more efficiently while the data amount is decreased and the processing load is suppressed from increasing.

In an embodiment of the present invention, the three-dimensional measurement device may further include a measurement result display portion displaying the measurement result. In the case where the re-measurement process guide portion is configured to provide a guide content in the measurement result display portion, the guide content is notified to the operator more clearly.

In an embodiment of the present invention, the three-dimensional measurement method may further include accepting a setting of the measurement range in the oral cavity or specifying a site in the oral cavity that does not need to be measured to accept a setting of the measurement range. With the above-described embodiment of the present invention, only a desired measurement range is measured. Therefore, the measurement is performed more accurately and more efficiently while the data amount is decreased and the processing load is suppressed from increasing.

A three-dimensional measurement method and a three-dimensional measurement device according to embodiments of the present invention prevent increase in a data amount and a processing load and provide a highly precise measurement result.

Obviously, numerous modifications and variations of the present invention are possible in light of the above teachings. It is therefore to be understood that within the scope of the appended claims, the invention may be practiced otherwise than as specifically described herein.

The invention claimed is:

1. A method of three-dimensional measurement in an oral cavity, comprising:
conducting three-dimensional measurement on a measurement range in the oral cavity;
detecting a measurement site in which measurement information is insufficient in a measurement result acquired in the three-dimensional measurement;
specifying a start position at which re-measurement on the measurement site detected is to be started;
re-measuring an area starting from the start position such that the area encompasses the measurement site; and
adapting at least one first characteristic site having first characteristic information in a re-measurement result from the re-measuring, and at least one second characteristic site having second characteristic information in the measurement result from the three-dimensional measurement with respect to each other such that three-dimensional measurement information is created on the measurement range, the first characteristic site and the second characteristic site being outside the measurement site in which measurement information is insufficient.

2. The method of claim 1, further comprising:
detecting an adaptable characteristic site with greater adaptability than other characteristic sites among the at least one second characteristic site based on the measurement result acquired in the three-dimensional measurement; and
specifying the adaptable characteristic site as the start position.

3. The method of claim 1, further comprising:
accepting a specification operation to specify the start position.

4. The method of claim 1, further comprising:
accepting a setting of a measurement precision for the measurement range,
wherein the detecting the measurement site includes detecting insufficiency of the measurement information, on a corresponding site, in the measurement result from the three-dimensional measurement based on the measurement precision.

5. The method of claim 1, further comprising:
guiding a re-measurement process in the re-measurement.

6. The method of claim 1, further comprising:
accepting a setting of the measurement range in the oral cavity or of specifying a site in the oral cavity that does not need to be measured to accept a setting of the measurement range.

7. The method of claim 2, further comprising:
accepting a setting of a measurement precision for the measurement range,
wherein the detecting the measurement site includes detecting insufficiency of the measurement information, on a corresponding site, in the measurement result from the three-dimensional measurement based on the measurement precision.

8. The method of claim 2, further comprising:
guiding a re-measurement process in the re-measurement.

9. The method of claim 2, further comprising:
accepting a setting of the measurement range in the oral cavity or of specifying a site in the oral cavity that does not need to be measured to accept a setting of the measurement range.

10. The method of claim 3, further comprising:
accepting a setting of a measurement precision for the measurement range,
wherein the detecting the measurement site includes detecting insufficiency of the measurement information, on a corresponding site, in the measurement result from the three-dimensional measurement based on the measurement precision.

11. The three-dimensional measurement apparatus according to claim 1, wherein the operation circuitry is configured to set the measurement range in the oral cavity or specify a site in the oral cavity that does not need to be measured to set the measurement range.

12. A three-dimensional measurement apparatus for an oral cavity, comprising:
a three-dimensional measurement device that conducts three-dimensional measurement on a measurement range in the oral cavity;
computation processing circuitry configured to detect a measurement site in which measurement information is insufficient in a measurement result acquired by the three-dimensional measurement device; and
output circuitry configured to specify a start position at which re-measurement on the measurement site detected is to be started,
wherein the computation processing circuitry is configured to adapt at least one first characteristic site having first characteristic information in a re-measurement result from the re-measurement by the three-dimensional measurement device on an area starting from the start position and encompassing the measurement site, and at least one second characteristic site having second characteristic information in the measurement result from the three-dimensional measurement with respect to each other such that three-dimensional measurement information is created on the measurement range, the first characteristic site and the second characteristic site being outside the measurement site in which measurement information is insufficient.

13. The three-dimensional measurement apparatus according to claim 12, wherein the computation processing circuitry is configured to detect an adaptable characteristic site with greater adaptability than other characteristic sites among the at least one second characteristic site based on the measurement result from the three-dimensional measurement on a measured area and specify the adaptable characteristic site as the re-measurement start position.

14. The three-dimensional measurement apparatus according to claim 12, wherein the computation processing circuitry is configured to specify the start position.

15. The three-dimensional measurement apparatus according to claim 12, further comprising:
operation circuitry configured to set a measurement precision for the measurement range,
wherein the computation processing circuitry is configured to detect insufficiency of the measurement information, on a corresponding site, in the measurement result on a measured area provided by the three-dimensional measurement device based on set measurement precision.

16. The three-dimensional measurement apparatus according to claim 12, wherein the output circuitry is configured to guide a re-measurement process by the three-dimensional measurement device.

17. The three-dimensional measurement apparatus according to claim 16, wherein the output circuitry is configured to display the measurement result, and to provide a guide display.

18. The three-dimensional measurement apparatus according to claim 13, further comprising:
operation circuitry configured to set a measurement precision for the measurement range,
wherein the computation processing circuitry is configured to detect insufficiency of the measurement information, on a corresponding site, in the measurement result on a measured area provided by the three-dimensional measurement device based on set measurement precision.

19. The three-dimensional measurement apparatus according to claim 13, wherein the output circuitry is configured to guide a re-measurement process by the three-dimensional measurement device.

20. The three-dimensional measurement apparatus according to claim 19, wherein the output circuitry is configured to display the measurement result, and to provide a guide display.

21. A three-dimensional measurement method for three-dimensionally measuring a desired measurement range in an oral cavity, comprising:
three-dimensionally measuring, a three-dimensional measurement step, the measurement range;
detecting, in a lack portion detecting step, a measurement information deficient portion where measured information in the measurement result is insufficient;
based on the measurement results of the three-dimensional measurement process, detecting a characteristic point, a portion containing the detected characteristic point;
designating, in a re-measurement start position designation step, a re-measurement start position;
notifying, in a re-measurement start position notification step, the re-measurement start position;
re-measuring, in a re-measurement step, from the re-measurement start position including the measurement information deficient portion;
matching a re-measurement result re-measured in the re-measurement step and the measurement result of the three-dimensional measurement step with a characteristic portion having a characteristic information in each measurement result; and
obtaining, in a three-dimensional measurement information creating step, the three-dimensional measurement information of the measurement range for performing a three-dimensional measurement information creation process.

22. The three-dimensional measurement method of claim 21, wherein the re-measurement start position notification step further includes reporting the measurement information deficient portion.

* * * * *